US010456235B2

(12) United States Patent
Tal et al.

(10) Patent No.: US 10,456,235 B2
(45) Date of Patent: Oct. 29, 2019

(54) EMBOLIZATION PARTICULATES FOR OCCLUDING A BLOOD VESSEL

(71) Applicant: ACCURATE MEDICAL THERAPEUTICS LTD., Tel-Aviv (IL)

(72) Inventors: Michael Gabriel Tal, Savyon (IL); Eran Miller, Moshav Beit Elazari (IL)

(73) Assignee: ACCURATE MEDICAL THERAPEUTICS LTD., Tel-Aviv (IL)

( * ) Notice: Subject to any disclaimer, the term of this patent is extended or adjusted under 35 U.S.C. 154(b) by 0 days.

(21) Appl. No.: 15/554,850

(22) PCT Filed: Mar. 2, 2016

(86) PCT No.: PCT/IB2016/051167
§ 371 (c)(1),
(2) Date: Aug. 31, 2017

(87) PCT Pub. No.: WO2016/139590
PCT Pub. Date: Sep. 9, 2016

(65) Prior Publication Data
US 2018/0028194 A1  Feb. 1, 2018

Related U.S. Application Data

(60) Provisional application No. 62/127,036, filed on Mar. 2, 2015.

(51) Int. Cl.
| | | |
|---|---|---|
| *A61F 2/01* | (2006.01) | |
| *A61B 17/12* | (2006.01) | |
| *A61M 25/00* | (2006.01) | |
| *A61K 9/00* | (2006.01) | |
| *A61K 9/16* | (2006.01) | |
| *A61K 31/704* | (2006.01) | |
| *A61L 24/00* | (2006.01) | |
| *A61L 24/02* | (2006.01) | |
| *A61M 5/00* | (2006.01) | |

(52) U.S. Cl.
CPC ........ *A61F 2/013* (2013.01); *A61B 17/12109* (2013.01); *A61B 17/12181* (2013.01); *A61B 17/12186* (2013.01); *A61K 9/0019* (2013.01); *A61K 9/1676* (2013.01); *A61K 31/704* (2013.01); *A61L 24/0015* (2013.01); *A61L 24/02* (2013.01); *A61M 25/0074* (2013.01); *A61B 2017/1205* (2013.01); *A61F 2002/011* (2013.01); *A61F 2002/016* (2013.01); *A61L 2300/23* (2013.01); *A61L 2300/416* (2013.01); *A61L 2430/36* (2013.01); *A61M 5/007* (2013.01); *A61M 25/007* (2013.01); *A61M 25/0021* (2013.01); *A61M 2025/0042* (2013.01)

(58) Field of Classification Search
None
See application file for complete search history.

(56) References Cited

U.S. PATENT DOCUMENTS

| | | | |
|---|---|---|---|
| 2005/0095428 A1* | 5/2005 | Dicarlo | A61K 49/0414 428/402 |
| 2007/0082021 A1 | 4/2007 | Bates | |
| 2010/0131002 A1 | 5/2010 | Connor et al. | |
| 2011/0048433 A1 | 3/2011 | Pfister | |
| 2012/0172908 A1 | 7/2012 | Grace | |
| 2015/0273071 A1* | 10/2015 | Green | C07C 323/12 424/497 |

FOREIGN PATENT DOCUMENTS

WO   2009134337   11/2009

OTHER PUBLICATIONS

International Search Report of PCT/IB2016/051167 Completed: Jun. 28, 2016; dated Jun. 29, 2016 4 pages.
Written Opinion of the International Searching Authority of PCT/IB2016/051167 Completed: Jun. 28, 2016; dated Jun. 29, 2016 6 pages.

* cited by examiner

*Primary Examiner* — Susan T Tran
*Assistant Examiner* — William Craigo
(74) *Attorney, Agent, or Firm* — The Roy Gross Law Firm, LLC; Roy Gross

(57) ABSTRACT

Injectable embolization particulates (e.g., particles, microstructures, beads) employed in embolization procedures, for facilitating blood vessel occlusion. Exemplary embolization particulates for occluding a blood vessel include a plurality of embolization beads, each bead having a plurality of outwardly protruding portions, wherein, upon a first one and a second one of the beads accumulating against a boundary of the blood vessel, protruding portions of the first bead are configured to intermesh with protruding portions of the second bead, so as to occlude the blood vessel. Also disclosed are compositions of embolization particulates including a plurality of shaped embolization beads, and methods for embolizing or occluding a blood vessel using embolization particulates or compositions thereof. Embolization particulates have particular shapes for facilitating blood vessel occlusion while preventing or diminishing back flow (reflux) of embolic material, and may be coated or impregnated with therapeutic agents or radioactive isotopes, for increasing desirable therapeutic effects.

18 Claims, 2 Drawing Sheets

EMBOLIZATION PARTICULATES FOR OCCLUDING A BLOOD VESSEL

RELATED APPLICATION

This application is a 35 U.S.C.§ 371 national phase application of PCT/IB2016/051167, filed Mar. 2, 2016, which claims the benefit of priority under 35 USC 119(e) of U.S. Provisional Patent Application 62/127,036, filed on Mar. 2, 2015 entitled "Emobilization Microcatheter and Uses Thereof", the contents of which are incorporated herein by reference in their entirety.

FIELD OF THE INVENTION

The present invention, in some embodiments thereof, relates to injectable embolization particulates (e.g., particles, microstructures, beads) employed in embolization procedures, for facilitating blood vessel occlusion. Some embodiments of the present invention further relate to compositions of the disclosed embolization particulates, and to methods for embolizing or occluding a blood vessel using the disclosed embolization particulates or compositions thereof.

BACKGROUND OF THE INVENTION

The technique of embolization involves the introduction of particles into the circulation to occlude blood vessels, for example, so as to either arrest or prevent hemorrhage, or to cut off blood flow to a tissue or an organ. Blood vessel occlusion is desirable for managing various diseases and conditions. An embolization procedure is typically associated with an insertion of a catheter or a microcathter (depending on the size of the target blood vessel) into a blood vessel and injection of an embolic agent through the catheter/microcatheter. The embolic agent is chosen, for example, based on the size of the vessel to be occluded, the desired duration of occlusion, or/and the type of disease or condition to be treated (e.g., hypervascular tumors, uterine fibroids, etc.), among other factors. Widely known embolic agents are oils, foam, plug, microspheres. or beads.

A follow-up angiogram may be performed to determine the specificity and completeness of an arterial occlusion. Blocking the blood supply to the tissue is intended to result in shrinkage or/and death of the tissue.

Embolization therapy is currently used to treat advanced liver cancer in patients that are not candidates for liver transplantation or liver resection. and also employed for treating other cancer types. There are currently numerous embolic therapies available. Exemplary therapies are trans-arterial embolization (or TAE), transarterial chemoembolization (TACE), drug eluting bead (DEB) therapy, and trans-arterial radioembolization (TARE).

TAE (also known as bland embolization) utilizes embolic particles injected into arteries feeding the tumor to stop blood flow to the tumor, thus causing necrosis. Typically, the embolic particles do not contain a drug.

TACE involves initial localized injections of a chemotherapeutic drug followed immediately by injection of embolic particles to prevent drug reflux and to cause embolization. TACE provides for both embolization (necrosis) of tumor cells and chemotherapy.

DEB involves combining/integrating an (elutable) drug into embolic particles, and similar to TACE involves two modes of action. In contrast to TACE, DEB provides sustained drug release. However, currently available DEB products show in-vitro rapid release (i.e., within hours) of the drug from the embolic particles. Also, current DEB therapy utilizes biostable particles, thereby precluding re-treatment. Embolic therapies are not curative, however, in most therapeutic situations, a single therapy delays tumor progression.

Trans-arterial radioembolization (TARE) involves (injective) administration of radioactively labeled microspheres into a blood vessel. The injected microspheres emit radiation to surrounding tissues which then undergo necrosis.

In spite of known teachings and practices in the field and art of the invention, there is an on-going need for developing new and improved injectable embolization particulates (e.g., particles, microstructures, beads), compositions thereof, and methods for using such in embolization procedures.

SUMMARY OF THE INVENTION

The present invention, in some embodiments thereof, relates to injectable embolization particulates (e.g., particles, microstructures, beads) employed in embolization procedures, for facilitating blood vessel occlusion. Some embodiments of the present invention further relate to compositions of the disclosed embolization particulates including a plurality of shaped embolization beads, and to methods for embolizing or occluding a blood vessel using the disclosed embolization particulates or compositions thereof.

According to an aspect of some embodiments of the present invention, there is provided embolization particulates suitable for occluding a blood vessel, the embolization particulates comprising: a plurality of embolization beads, each of the embolization beads comprises: a plurality of outwardly protruding portions, wherein, upon a first one and a second one of the embolization beads accumulating against a boundary of the small blood vessel, the protruding portions of the first embolization bead are configured to intermesh with the protruding portions of the second embolization bead, so as to occlude the blood vessel.

According to an aspect of some embodiments of the present invention, there is provided an embolization bead suitable for occluding a blood vessel, the embolization bead comprising: a plurality of outwardly protruding portions, wherein, upon a first one and a second one of the embolization beads accumulating against a boundary of the small blood vessel, the protruding portions of the first embolization bead are configured to intermesh with the protruding portions of the second embolization bead, so as to occlude the blood vessel.

According to some embodiments of the invention, the embolization beads are configured to resist or/and dissipate forces generated by, or originating from, fluid flow during an embolization procedure. According to some embodiments of the invention, at least one of the outwardly protruding portions is hydrodynamically shaped to facilitate laminar or/and unhindered flow there around and to diminish impact of incoming fluid flow directed thereto.

According to some embodiments of the invention, the embolization beads have three outwardly protruding portions. According to some embodiments of the invention, the embolization beads have a tetrapod-like shape. According to some embodiments of the invention, at least one of the outwardly protruding portions has a tetrahedron or tetrahedron-like shape. According to some embodiments of the invention, at least one of the outwardly protruding portions includes at least one concavity. According to some embodiments of the invention, at least one of the outwardly protruding portions includes at least one hole passing through the outwardly protruding portion. According to some embodiments of the invention, at least one concavity or/and the hole is filled with a therapeutic agent.

According to some embodiments of the invention, the embolization beads are prepared from a glass, a metal, a polymer, or a combination thereof. According to some embodiments of the invention, the embolization beads have a diameter in a range of between about 5 micrometers and about 500 micrometers, or in a range of between about 5 micrometers and about 100 micrometers, wherein the diameter is measured between external surfaces of two opposing protruding portions of one of the embolization beads.

According to an aspect of some embodiments of the present invention, there is provided a composition comprising: the embolization particulates, and a pharmaceutically acceptable excipient or carrier. According to some embodiments of the invention, the composition further comprises a contrasting agent or a therapeutic agent. According to some embodiments of the invention, the contrasting agent is selected from the group consisting of tantalum, tantalum oxide, and barium sulfate. According to some embodiments of the invention, the therapeutic agent is a chemotherapeutic agent.

According to an aspect of some embodiments of the present invention, there is provided a method for embolizing or occluding a blood vessel in a subject, the method comprising: injecting into the blood vessel a sufficient amount of the embolization particulates, or of a composition thereof, thereby allowing the embolization beads to aggregate into a chosen aggregated structure prior to or/and during embolization. According to some embodiments of the invention, the blood vessel feeds a tumor or an arteriovenous malformation.

According to an aspect of some embodiments of the present invention, there is provided the embolization particulates, or a composition thereof, for use in embolizing a blood vessel feeding a tumor or an arteriovenous malformation.

According to an aspect of some embodiments of the present invention, there is provided a method of treating a disease or disorder that may benefit from occluding a blood vessel feeding an organ associated with the disease or disorder, the method comprising: injecting into the blood vessel a sufficient amount of the embolization particulates, or of a composition thereof. According to some embodiments of the invention, in the method, the disease or disorder is selected from: cancer, an arteriovenous malformation, and hemorrhage.

According to an aspect of some embodiments of the present invention, there is provided the embolization particulates, or a composition thereof, for use in treating a disease or disorder that may benefit from occluding a blood vessel feeding an organ associated with the disease or disorder. According to some embodiments of the invention, the disease or disorder is selected from: cancer, arteriovenous malformations, and hemorrhage.

Unless otherwise defined, all technical or/and scientific terms used herein have the same meaning as commonly understood by one of ordinary skill in the art to which the invention pertains. Although methods and materials similar or equivalent to those described herein can be used in the practice or testing of embodiments of the invention, exemplary methods or/and materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
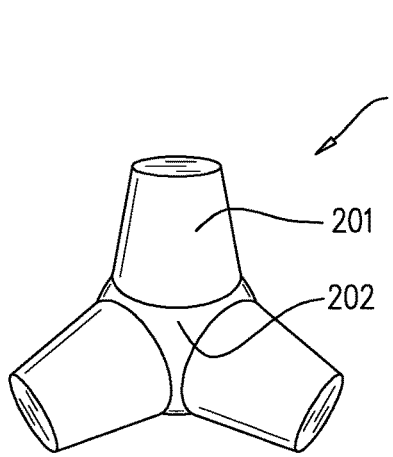
FIG. 1 is a schematic perspective view of an exemplary embodiment of an embolization bead having three protruding portions extending from the center of the bead, in accordance with some embodiments of the invention.

The present invention, in some embodiments thereof, relates to injectable embolization particulates (e.g., particles, microstructures, beads) employed in embolization procedures, for facilitating 20 blood vessel occlusion. Some embodiments of the present invention further relate to compositions of the disclosed embolization particulates including a plurality of shaped embolization beads, and to methods for embolizing or occluding a blood vessel using the disclosed embolization particulates or compositions thereof.

There is still a need to prevent, or at least diminish, possibility of non-target embolization or/and non-target deposition of embolization particulates (particles, microstructures, beads) which can adversely affect non-target locations or/and organs of a subject. Such undesirable non-target embolization or/and particulate deposition may occur by infiltration of embolization particulates from a target embolization site to a non-target location, for example, via body vasculature or/and abnormal shunts.

A possible way to prevent, or at least diminish, such undesirable side effects from occurring during embolization procedures, is to develop means which enable embolization particulates, for example, via their inherent characteristics and behavior, to aggregate (i.e., gather, collect, or combine together) under local conditions (such as flow rate, flow pressure, among other possible conditions) during an embolization process. Accordingly, it may be advantageous to provide new and improved vascular embolic materials, such as embolization particulates (e.g., in the form of particles, microstructures, beads), which may facilitate safer and more efficient occlusion of a blood vessel.

For example, according to some embodiments of the disclosed invention, the embolization particulates, for example, in the form of beads, are characterizable by a particular shape that may advantageously facilitate blood vessel occlusion while preventing, or at least diminishing, back flow (i.e., reflux) of embolic material. According to some embodiments of the invention, the embolization particulates, for example, in the form of beads, may be coated or impregnated with a therapeutic agent, or with a radioactive isotope, for increasing one or more desirable therapeutic effects.

The terms "embolization" and "embolizing" are herein used in conjunction with the terms "embolization material" and "embolization therapy", and refer to a process wherein a medicinal substance or material injected into a blood vessel hardens, fills, plugs, or/and occludes the blood vessel or/and encourages clot formation so that blood flow through the vessel ceases. Blood vessel embolization is useful in preventing/controlling bleeding (e.g., organ bleeding, gastrointestinal bleeding, vascular bleeding, bleeding associated with an aneurysm), or as a treatment of a disease (e.g., cancers) by preventing its blood supply.

The terms "aggregation" and "aggregated" are herein used in conjunction with the term "aggregated structure", and refer to a process wherein a particulate mass (e.g., in a form of infusion suspension of beads) assembles into a concentrated depot, being more concentrated or/and dense than concentration/density of the infusion suspension at exit of distal outlet (infusion opening) of the embolization catheter. Such a particulate mass (concentrated depot) is characterized by at least some of its particles physically (mechanically) or/and chemically interconnecting among themselves. In some embodiments of the invention, particle (inter-particle) aggregation may be considered as a preliminary stage before creation of a local emboli in a blood vessel. In some embodiments, the unique shape or/and weight distribution in a bead, according to embodiments of the invention, improves its inherent ability to resist aggregation or/and concertation at a too early stage of the embolization delivery process (e.g., close to distal outlet of the embolization catheter or/and at relatively high blood flow rate), so that a farther distal arterial occlusion can be achieved. Optionally, additionally or alternatively, the unique shape or/and weight distribution in a bead, according to embodiments of the invention, improves its inherent ability to increase likelihood, strength, density, or/and concertation of a final aggregation in a mature stage of the embolization delivery process (e.g., relatively distant from distal outlet of the embolization catheter or/and at relatively low blood flow rate), in order to diminish likelihood/quantity of beads (particles) non-target deposition phenomenon.

The term "bead" is herein used in conjunction with "particle" or "particulate", and refers to a substance, for example, in the form of a minute portion or a fragment of material, that may be formed from a variety of materials (e.g., a glass, a polymer, a metal), and have characteristic sizes (lengths, widths, diameters) in an exemplary range of between about 10 microns (micrometers) and about 1,000 microns (micrometers), and may be suitable for medical applications (e.g., occluding a blood vessel), for example, for delivery as a suspended material in an infusion suspension.

An aspect of some embodiments of the invention is provision of embolization particulates (in a form of particles, microstructures, or beads) suitable for occluding a blood vessel. In exemplary embodiments, the embolization particulates include a plurality of embolization beads, with each of the embolization bead having a plurality of outwardly protruding portions, wherein, upon a first one and a second one of the embolization beads accumulating against a boundary of the small blood vessel, the protruding portions of the first embolization bead are configured to intermesh with the protruding portions of the second embolization bead, so as to occlude the blood vessel.

According to an aspect of some embodiments of the present invention, there is provided an embolization bead suitable for occluding a blood vessel, the embolization bead comprising: a plurality of outwardly protruding portions, wherein, upon a first one and a second one of the embolization beads accumulating against a boundary of the small blood vessel, the protruding portions of the first embolization 15 bead are configured to intermesh with the protruding portions of the second embolization bead, so as to occlude the blood vessel.

An aspect of some embodiments of the invention is provision of a composition including the embolization particulates and a pharmaceutically acceptable excipient or carrier.

An aspect of some embodiments of the invention is provision of a method for embolizing or occluding a blood vessel in a subject, the method including: injecting into the blood vessel a sufficient amount of the embolization particulates, or of a composition thereof, thereby allowing the embolization beads to aggregate into a chosen aggregated structure prior to or/and during embolization. An aspect of some embodiments of the invention is provision of a method of treating a disease or disorder that may benefit from occluding a blood vessel feeding an organ associated with the disease or disorder, the method including: injecting into the blood vessel a sufficient amount of the embolization particulates, or of a composition thereof. An aspect of some embodiments of the invention is provision of the embolization particulates, or a composition thereof, for use in treating a disease or disorder that may benefit from occluding a blood vessel feeding an organ associated with the disease or disorder.

The preceding aspects of exemplary embodiments of the present invention, and characteristics and features thereof, are better understood with reference to the following illustrative description and accompanying drawings. Throughout the following illustrative description and accompanying drawings, same reference notation and terminology (i.e., numbers, letters, symbols) are consistently used and refer to same structures, components, elements, steps or procedures, or/and features.

It is to be understood that the invention is not necessarily limited in its application to particular details of construction of the embolization particulates (or embolization beads thereof), or to any particular sequential ordering of method steps or procedures, set forth in the following illustrative description. The invention is capable of other embodiments or of being practiced or carried out in various ways. For example, the following exemplary embodiments may be described in the context of exemplary embolization procedures for ease of description and understanding. However, the invention may be adapted to various clinical applications without departing from the overall scope of the invention, for example, any local injected deposition of a pharmaceutical or non-pharmaceutical particulates within a bodily lumen.

Morphological/Structural Characteristics, Properties, and Features of the Embolization Particulates (Beads)

In exemplary embodiments, the embolization beads of the invention include a plurality of outwardly protruding portions, wherein outwardly protruding portions of a first bead are configured to intermesh with outwardly protruding portions of a second bead. The beads may have various shapes, as long as the beads are capable of intermeshing with each other and block blood flow. In exemplary embodiments, the beads may be symmetric or asymmetric. In exemplary embodiments, the embolization bead is having two or more, three or more, four or more, five or more, or six or more protruding portions. In exemplary embodiments, the beads protruding portions may extend from the central portion of the bead. In exemplary embodiments, the beads have a spherical body and the protruding portions may extend from the central spherical portion of the bead. In exemplary embodiments, the beads have a body with an elongated shape and the protruding portions may extend from any portion of the bead body. In exemplary embodiments, the embolization beads have a tetrapod-like shape. In exemplary embodiments, at least one of the outwardly protruding portions has a multi-faced type shape, for example, a tetrahedron (tetrahedral) or tetrahedron-like (tetrahedral-like) shape. In exemplary embodiments, at least one of the outwardly protruding portions includes at least one concavity. In exemplary embodiments, at least one of the outwardly protruding portions includes at least one hole passing through the outwardly protruding portion.

Figure 2:
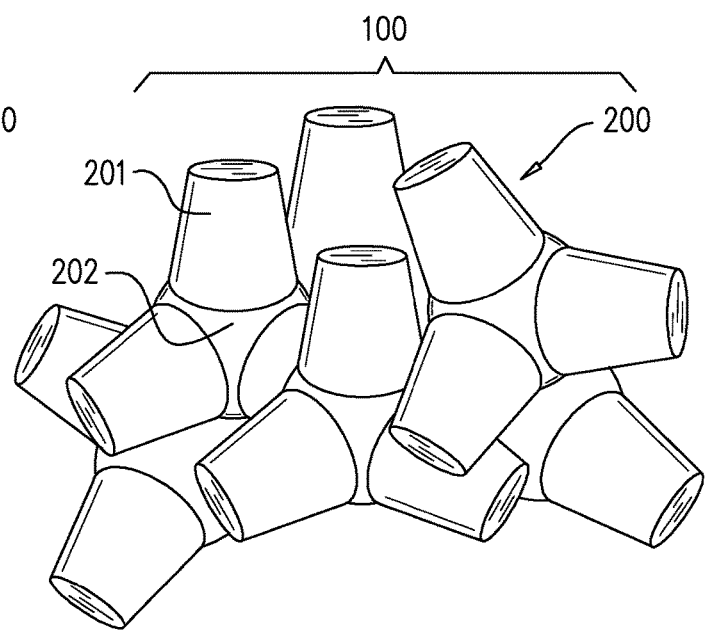
FIG. 2 is a schematic perspective view of an exemplary embodiment of embolization particulates as an aggregation of a plurality of the embolization bead of FIG. 1, particularly highlighting intermeshing (engaging) of protruding portions of several embolization beads, in accordance with some embodiments of the invention.

Reference is now made to the drawings. FIG. 1 schematically illustrates a perspective view of an exemplary embolization bead 200 having exemplary bead protruding portions 201. FIG. 2 schematically illustrates a perspective view of an exemplary embodiment of embolization particulates, for example, as an aggregated structure 100 of a plurality of exemplary embolization beads 200 (of FIG. 1), particularly highlighting intermeshing (engaging) of embolization bead protruding portions 201.

In exemplary embodiments, embolization bead 200 is configured for creating an embolus during an embolization procedure, and includes a plurality of outwardly protruding portions 201. Embolization bead 200 may have a substantially spherical body, for example, spherical body 202 shown in FIGS. 1 and 2, and the outwardly protruding portions 201 may extend from the spherical body 202. In FIGS. 1 and 2, embolization beads 200 are illustrated having three protruding portions 201, but may have a different number of protruding portions (e.g., two, or four, or more protruding portions).

In exemplary embodiments, during the course of injecting the beads within a blood vessel and prior to accumulation of a plurality of the beads into an aggregated structure, such as aggregated structure 100, at least one of the outwardly protruding portion 201 is hydrodynamically shaped to facilitate laminar or/and unhindered flow there around and to diminish impact of incoming fluid flow directed thereto.

In exemplary embodiments, embolization bead 200 is also configured, based on its design and dimensions, such that whereupon at least a first and a second thereof, accumulating against a boundary of a target bodily part within a small blood vessel, for example, feeding a target bodily part, the protruding portions of a first embolization bead will have an increased probability to intermesh with the protruding portions of a second embolization bead (as shown, in an exemplary non-limiting manner, in FIGS. 2 and 5), optionally particularly at low (e.g., close to null) blood flow rates.

In some embodiments, aggregated structure 100 or/and embolization bead 200 is further configured to resist or/and dissipate forces generated by or originating from fluid flow during the embolization procedure.

In exemplary embodiments, embolization bead 200 has, or is similar at least in part to, a tetrapod-like shape. Optionally, at least one outwardly protruding portion 201 has a multi-faced type shape, for example, a tetrahedron (tetrahedral) or tetrahedron-like (tetrahedral-like) shape. Optionally, at least one outwardly protruding portion 201 includes at least one concavity or/and at least one hole passing therethrough the outwardly protruding portion, which, optionally, is filled with a pharmaceutical agent.

Figure 3:
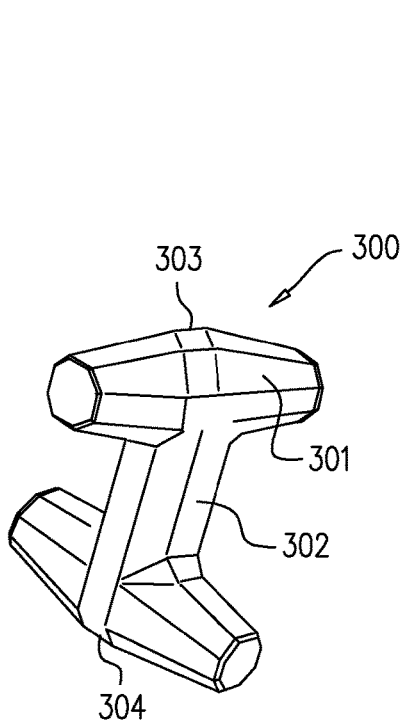
FIG. 3 is a schematic perspective view of an exemplary embodiment of an embolization bead having four protruding portions, each two protruding portions extending from opposite sides of a bead end, in accordance with some embodiments of the invention.
Figure 4:
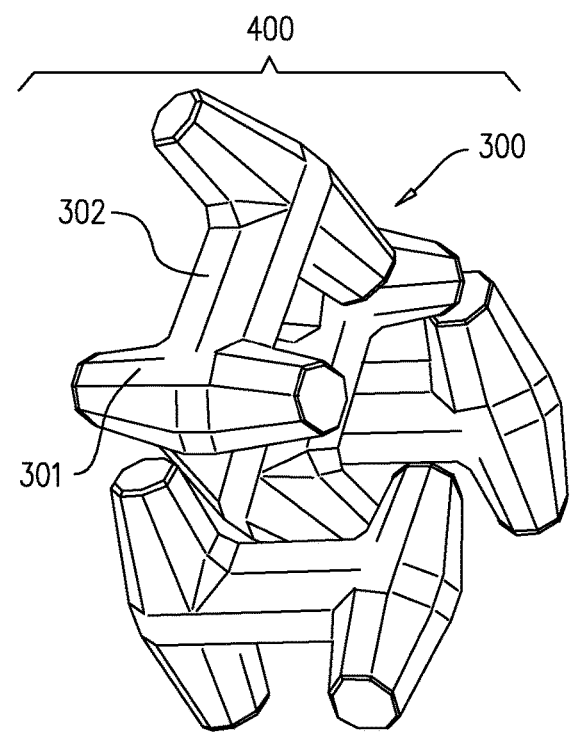
FIG. 4 is a schematic perspective view of an exemplary embodiment of embolization particulates as an aggregation of a plurality of the embolization bead of FIG. 3, particularly highlighting intermeshing (engaging) of protruding portions of several embolization beads, in accordance with some embodiments of the invention.

FIG. 3 schematically illustrates a perspective view of an exemplary embolization bead 300 having exemplary bead protruding portions 301. FIG. 4 schematically illustrates a perspective view of an exemplary embodiment of embolization particulates, for example, as a aggregated structure 400 of a plurality of exemplary embolization beads 300, particularly highlighting intermeshing (engaging) of embolization bead protruding portions 301.

In exemplary embodiments, embolization bead 300 is configured for creating an embolus during an embolization procedure, and includes a plurality of outwardly protruding portions 301. Embolization bead 300 includes a first bead end 303, a second bead end 304, and a bead body 302 extending between the first bead end 303 and the second bead end 304. Two outwardly protruding portions 301 oppositely extend from the first bead end 303, and two outwardly protruding portions 301 oppositely extend from the second bead end 304. Embolization beads 300 are illustrated having four protruding portions, but may also have a different number of protruding portions (e.g., two, three, five, or more protruding portions). Protruding portions 301 of embolization bead 300, extending from the first bead end 303 may be disposed to form any angle in a range of between about 180 degrees and about 0 degrees with respect to protruding portions 301, extending from the second bead end 304.

Figure 5:
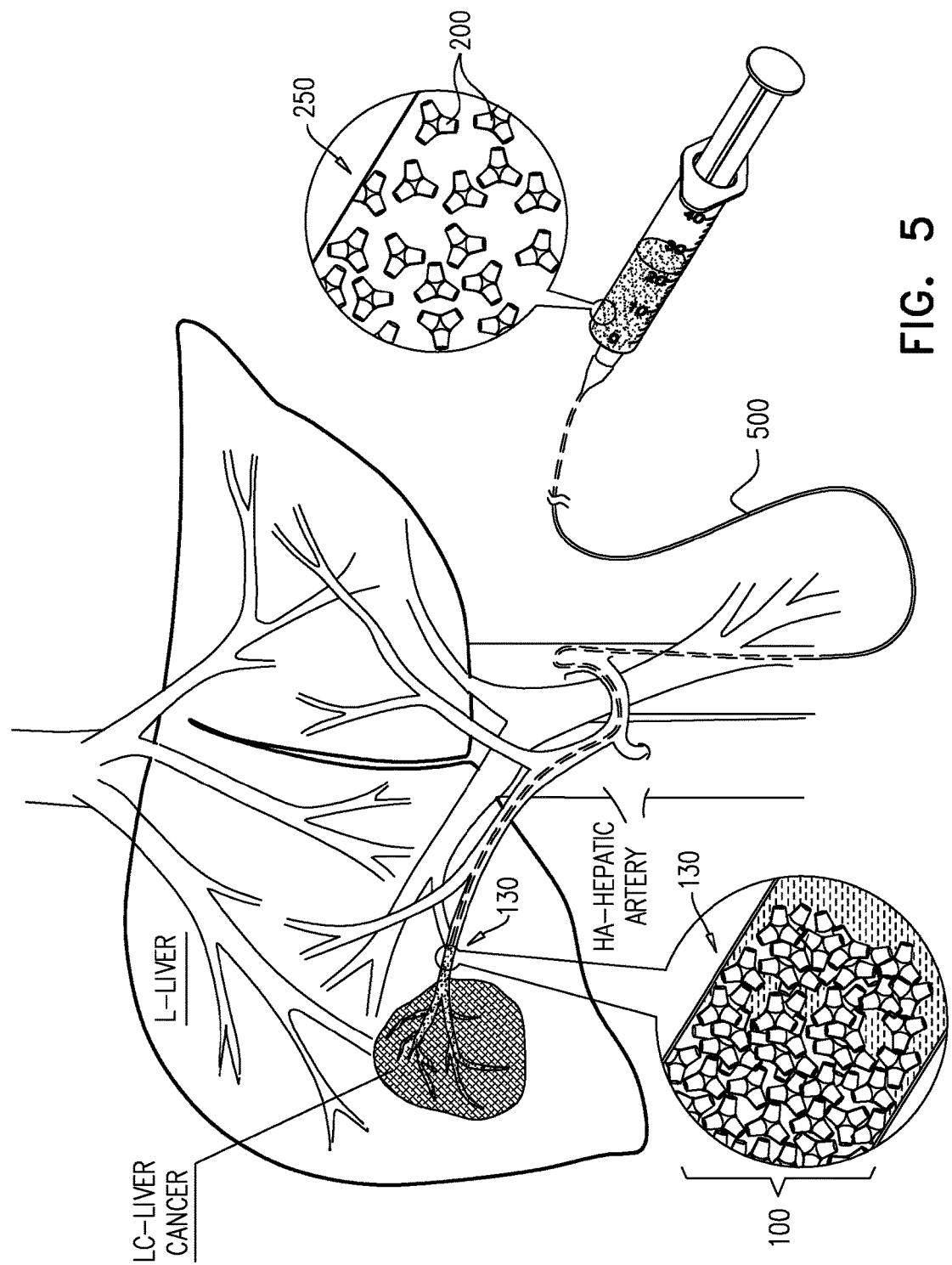
FIG. 5 is a schematic presentation of an exemplary suspension of embolization particulates (as embolization beads of FIGS. 1 and 2), following injection into a blood vessel (e.g., a hepatic artery) feeding a tumor within the liver, and engaging to form a dense aggregated structure before or/and during an embolization process, so as to form an embolus within the blood vessel, thereby occluding the blood vessel, in accordance with some embodiments of the invention.

Embolization bead 300 is also configured, based on its design and dimensions, such that whereupon at least a first and a second thereof, accumulating against a boundary of a target bodily part within a small blood vessel, feeding the target bodily part, the protruding portions of the first embolization bead shall have an increased probability to intermesh with the protruding portions of the second embolization bead (as shown, for demonstrative purposes only, in FIGS. 4 and 5).

In some embodiments, embolization bead 300 is further configured to resist or/and dissipate forces generated by or originating from fluid flow during the embolization procedure. In exemplary embodiments, at least one outwardly protruding portion 301 has a multi-faced type shape, for example, a tetrahedron (tetrahedral) or tetrahedron-like (tetrahedral-like) shape. Optionally, at least one outwardly protruding portion 301 includes at least one concavity or/and at least one hole passing therethrough the outwardly protruding portion, which, optionally, is filled with a pharmaceutical agent.

In exemplary embodiments, the embolization beads may be prepared in various sizes. The embolization bead diameter sizes (when measured to extend between two opposite protrusions) may vary and range between 10 microns (μm)

and 1,500 microns, between 10 microns and 1,200 microns, between 10 microns and 1,000 microns, between 100 microns and 900 microns, between 10 microns and 500 microns, between 10 microns and 100 microns, between 10 microns and 50 microns, between 50 microns and 100 microns, between 100 microns and 300 microns, between 300 microns and 500 microns, between 500 microns and 700 microns, or between 700 microns and 900 microns.

The size and shape of the embolization beads may be measured by any method known in the art. For example, microscopic equipment (such as, Leica DM IRB (Leica) microscope equipped by Evolution MP Color CCD Camera (Media Cybernatics)) may be used. The analysis of size may be performed by Image Pro Plus™ (Media Cybernatics). An electron microscope (such as, scanning electron microscope (SEM)) to obtain a sample's surface topography and composition may be used.

In exemplary embodiments, the embolization beads are prepared from a material such as, but not limited to, a polymer, a metal, a glass, a ceramic material or any combination thereof. When a metal is used for the preparation of the embolization beads, visualization of the embolic material under X-ray radiation may be facilitated. Exemplary glass embolization beads are, without limitation, silicon dioxide ($SiO_2$), sodium oxide ($Na_2O$), sodium carbonate ($Na_2CO_3$), calcium oxide (CaO), or any combination thereof. Exemplary polymers suitable for implementing embodiments of the invention include, without limitation, polyvinyl alcohol (PVA), polytetrafluoroethylene (PTFE), carboxymethyl chitosan (CCN), carboxymethyl cellulose (CMC), 2-acrylamido-2-methyl-1-1-propane-sulphonoc acid (AMPS), poly(lactide-co-glycolide) (PLCG), poly(L-lactic acid) (PLLA), trisacrylgelatin having a coating of collagen, or any combination thereof. The polymer used may be chosen to have an appropriate molecular weight. In an exemplary embodiment, and when PVA is the polymer of choice, the PVA may have a molecular weight within the range of about 50,000 Da and about 300,000 Da. Suitable metals include, without limitation, silver, gold, palladium, platinum, tantalum (e.g. tantalum oxide), tungsten, iridium, titanium, magnesium, Strontium, Zinc, Lanthanum, barium (e.g. barium sulfate), and stainless steel. In an exemplary embodiment, a metal that may be used in preparing the embolization beads may include, without limitation, $TiO_2$, Pt or a mixture thereof. In a further exemplary embodiment, the glass embolization beads may be made from a combination of metals and glass and may include one or more of: zinc (e.g., ZnO), Lanthanum (e.g., $La_3O_2$), Titanium (e.g., $TiO_2$), Magnesium (e.g., MgO), Strontium (e.g., SrO) and sodium (e.g., $Na_2O$).

In exemplary embodiments, the embolization beads have a weight that vary and depend on the material used for producing the bead. The embolization bead weight may be uniform within the entire bead, or may be non-uniform having a center-of-mass not necessarily same as geometric center. Non-uniform embolization bead weight may be controlled or produced by combining at least two materials each having a different weight and producing the beads to include those material in a non-homogenous fashion.

In exemplary embodiments, and in order to further enhance the therapeutic effect (i.e. treating cancer), the embolization beads may also include an isotope, thus allowing delivery of β-ray or/and γ-ray. Suitable isotopes that may be incorporated or impregnated to the embolization beads of the invention, include, without limitation, yttrium-90 (Y90), rhenium-188 ($^{188}Re$), $^{99}mTc$, $^{32}P$, $^{166}Ho$, $^{109}Pb$, $^{140}La$ $^{153}Sm$, $^{165}Dy$, and $^{169}Er$.

According to further embodiments, and in order to further enhance the therapeutic effect (e.g., in treating cancer), the embolization beads may also include a therapeutic agent. Suitable exemplary therapeutic agents that may be incorporated to the embolization beads of the invention, include, without limitation, a chemotherapeutic agent, a peptide or polypeptide or any other chemical moiety or entity having a therapeutic effect. An exemplary chemotherapeutics that may be incorporated into the embolization beads of the invention, include, for example, paclitaxel, doxorubicin, nemorubicin hydrochloride (a derivative of doxorubicin).

Methods of Producing/Manufacturing the Embolization Particulates (Beads)

An aspect of some embodiments of the present invention relates to a method for producing embolization beads according to the embodiments of the invention.

The method includes homogenously admixing together the components from which the embolization beads are to be prepared and pouring a liquid mixture to a premade scaffold or mold. The method further includes, removing the molded particulates.

In an exemplary embodiment, and when the embolization beads are prepared from metals, or glass or a combination thereof, the process for preparing the embolization beads include, weighing and preparing a homogenous mixture of powders and melting the powders to form the desired composition. The purity of each raw material is, for example, greater than 90%. After either dry or wet mixing of the powders to achieve a homogeneous mixture, the mixture may be placed for melting (e.g., in a platinum crucible). The crucibles containing the powdered batch are heated to 1500° to 1600° C., depending upon the composition, by a furnace. In this temperature range, the batch melts to form a liquid which is stirred several times to decrease its chemical heterogeneity. The melt should remain at 1500° to 1600° C. until all solid material in the batch is totally dissolved (usually 2-5 hours being sufficient). When melting and stirring is complete, the crucible is removed from the furnace and the melt is quickly quenched to a glass by pouring the melt onto a cold mold or scaffold.

The final step is to examine a representative sample of the embolization beads in a scanning electron microscope to evaluate the size range and shape of the beads. A composition of the embolization beads can be checked by energy dispersive x-ray analysis to confirm that there is no chemical contamination. The embolization beads are packaged dry in clean containers and sterilized (for example, using 30 kGy gamma irradiation).

In exemplary embodiments, the obtained embolization beads are treated to incorporate a therapeutic agent. The embolization beads in accordance with this embodiment act as carriers of the therapeutic agent. The therapeutic agent may be incorporated to the embolization beads of the invention, in any method known in the art. The therapeutic agent may be included within holes formed in the embolization beads or within concavity shapes based on the surface of the protruding portions.

Methods for coating the embolization beads with a therapeutic agent include, without limitation, immersion coating, spray coating, and spin coat administration. Immersion coating of therapeutic agent includes impregnating surface of interest of the embolization beads with the therapeutic agent.

For example, coating may be performed by dissolving the therapeutic agent at a desired concentration that represents clinically applicable doses, admixing the therapeutic agent with the embolization beads and incubating those substances for a period of from a few minutes to a few hours. Drug release may be evaluated following incubation in an aqueous solution (Phosphate Buffer Saline (PBS)) or human plasma from human subjects for a few days.

Methods of Using the Embolization Particulates (Beads)

According to an aspect of the invention, there is provided a method for embolizing or occluding a 5 blood vessel in a subject in need thereof, the method including injecting into the blood vessel a sufficient amount of embolization beads of the invention, thereby allowing the embolization beads to aggregate into an aggregated structure prior to or/and during embolization.

According to yet another aspect of the invention, there is provided a method of treating a disease or disorder that may benefit from occluding a blood vessel feeding an organ associated with the disease or disorder, the method including injecting into the blood vessel a sufficient amount of embolization beads of the invention.

As used herein, the term "embolizing" as used in conjunction with the term "occluding" refers to creating an embolus or clot within a blood vessel.

As used herein, the term "treating" encompasses substantially ameliorating, relieving, alleviating and preventing symptoms of the disease in a patient in need thereof.

As used herein, the term "injecting" is interchangeable with the term "administering" and refers to the delivery of a suspension of the disclosed embolization beads within a blood vessel.

The embolization beads are particularly useful in occluding small blood vessels (such as capillaries). The embolization beads are useful to treat any disease condition or illness which may benefit, abolished, or ablated by colluding a blood vessel within the body or that feeds the diseased or afflicted body organ.

The embolization beads may be used in conjunction with a transarterial chemoembolization (TACE), drug eluting bead (DEB) therapy and radio-embolization. As used herein the term "a disease or disorder that may benefit from occluding a blood vessel feeding an organ associated with the disease or disorder" refers to any disease, disorder, or condition that may be treated with embolization material to abolish or relief symptoms associated with the disease, disorder, or condition. The term is interchangeable with the term "a disease or disorder amenable to an embolization therapy".

In exemplary embodiments, the embolization beads may be used to treat angiogenesis-dependent diseases (i.e., those diseases which require or induce vascular growth). Amongst such angiogenesis-dependent diseases the most prominent is cancer. Suitable cancers include, without limitation, a cancer that has spread (metastasized) to the liver from a primary tumor elsewhere (e.g., colorectal cancer, breast cancer, lung cancer and neuroendocrine tumors), cancer originating in the liver (such as hepatocellular carcinoma and cholangiocarcinoma), renal tumors (benign and malignant), tumor within the uterine (e.g., uterine fibroid), brain, central nervous system, kidneys, gall bladders, head and neck, oral cavity, thyroid, skin, mucous membranes, glandular organs, blood vessels, bone tissues, lymph nodes, lungs, esophagus, stomach, lacteal glands, pancreas, eyes, nasopharynge, womb, ovaries, endometrium, cervix, prostate gland, bladders, colon and rectum. For example, metastatic colorectal cancer in the liver and hepatocellular carcinoma are the cancers most often considered for radioembolization treatment. In exemplary embodiments, the embolization beads are used to prevent/control bleeding (e.g., organ bleeding, gastrointestinal bleeding, vascular bleeding, bleeding associated with an aneurysm). For example, the embolization beads are applicable to treat: hemorrhage (such as hemorrhage associated with pelvic fracture).

In exemplary embodiments of the present invention, there is provided a method of treating a condition or disease, using the embolization beads of the invention. A composition including the embolization beads, which is for example, administered to a patient in need of an embolization therapy having a tumor, for instance a hepatocellular carcinoma, is firstly prepared. The embolization beads may be administered alone or along (usually after) administration of a composition including a therapeutic agent (e.g. chemotherapeutics). The embolization beads may be administered when bound to a chemotherapeutic agent. It is often desirable for the suspension to be mixed prior to delivery with an imaging agent such as a conventional radio-opaque agent.

The compositions for administration are thus prepared according to the therapy of interest. The embolization beads may be loaded with the appropriate dose of a therapeutic agent just prior to administration or may be preloaded and ready for immediate use. When the embolization beads are coated with a therapeutic agent just prior to administration, the appropriate dose of the therapeutic agent, may be dissolved in adequate solution, and is then mixed with a suitable amount of beads. The pharmaceutical composition containing the therapeutic agent bound to embolization beads may allow a fast loading (about 1-2 h incubation) and a loading rate of the therapeutic agent into the beads (>99%) able to guarantee an easy administration of therapeutic doses to patients. The reconstituted therapeutic agent solution must be added to the embolization beads and agitated gently to encourage mixing.

The selection of the size of the embolization beads is based on the vascular target/vessel size.

A delivery catheter/microcatheter must be introduced into the target vessel according to standard interventional radiology technique. The embolization must be monitored under fluoroscopic visualization by adding a desired amount of contrast medium (such as a conventional radio-opaque agent) to a suspension fluid containing the embolization beads.

In exemplary embodiments, the embolization beads are slowly injected into the delivery catheter/microcatheter under fluoroscopic visualization while observing the contrast flow rate. Upon completion of the treatment, the catheter/microcatheter is removed while maintaining gentle suction so as not to dislodge embolization beads still within the catheter/microcatheter lumen. The embolic composition as administered to the patient in need of embolization therapy, may be delivered as a single one-off dosage. It may be found to be desirable for subsequent doses of an embolic composition useful in the invention, to be delivered at a time interval after the previous dose, for instance to embolise newly formed blood vessels supplying a tumor (e.g. after 4 to 12 weeks from the previous treatment).

Reference is now made to FIG. 5 which schematically illustrates an exemplary method of performing an embolization therapy, to treat a liver cancer (LC), utilizing a suspension 250 comprising an infusion fluid and embolization beads (e.g., beads 200) of the present invention. The embolization beads are configured to engage to form, following injection to a blood vessel (i.e., Hepatic Artery; HA) an aggregated structure (similar or identical to aggregated structure 100 of FIGS. 1 and 2) before or/and during embolization process for forming an embolus within the blood vessel, resulting with occluded blood vessel portion 130. The method includes, utilization of embolization beads 200 of the invention, but may be applicable to any of the aforementioned embolization beads, in accordance with the embodiments of the invention.

Embolization beads 200 may be used in conjunction with any suitable technique or/and procedure of embolization therapy (e.g., TAE, TACE, TARE) and may be introduced within a blood vessel feeding a tumor with any know and suitable catheter. For example, when the beads are provided with a radioactive isotope the technique is referred to as TARE. When the beads are injected thereafter a chemotherapeutic agent administration, the technique is referred to as TACE. When a therapeutic agent is coated within the beads, the technique is referred to as DEB (or DEB-TACE), and when the beads are provided without any substance, the technique may be referred to as TAE (or bland embolization).

Typically, for treating liver cancer, a catheter (a thin and flexible tube) is introduced through a small cut in the inner thigh and threaded up into the hepatic artery (HA) in the liver (L). A contrast enhancement material is usually injected into the bloodstream at this time to assist in monitoring the path of the catheter via angiography. Once the catheter is in positioned as appropriate, embolization beads 200 are injected into the artery. Once accumulated in the blood vessels, embolization beads 200 are arranged such that protruding portions of a first embolization bead 200 intermesh with protruding portions of a second embolization bead 200. Multiple embolization beads 200, thus create emboli within boundaries of a blood vessel, blood supply to the tumor is diminished, effecting tumor starvation and necrosis.

Pharmaceutical Compositions Including the Embolization Particulates (Beads)

According to yet another aspect, the present invention also provides pharmaceutical compositions including the herein disclosed embolization beads, and a pharmaceutical acceptable carrier or excipient.

The term "pharmaceutical composition", as used herein, encompasses formulated preparations including the herein disclosed embolization beads, and one or more pharmaceutically acceptable excipients, diluents or carriers.

The term "pharmaceutically acceptable", as used herein, means approved by a regulatory agency of a federal or a state government or listed in a recognized pharmacopeia for use in humans or animals.

The term "carrier", as used herein, refers to a diluent, adjuvant, excipient, or vehicle with which the therapeutic is administered. Such pharmaceutical carriers can be sterile aqueous liquids (e.g., saline, or PBS) or, oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The carrier(s) must be "acceptable" in the sense of being compatible with the other ingredients of the composition and not deleterious to the recipients thereof.

The composition including the embolization beads is typically referred to as a suspension. The suspension may be an infusion suspension comprising the beads and an infusion fluid (i.e., pharmaceutically acceptable excipients, diluents or carriers). In exemplary embodiments, the embolization beads may have a relatively low specific gravity. The embolization beads thus benefit from a buoyancy effect for reduced energy expenditure and prevent sedimentation when provided within a pharmaceutical composition or/and when injected within the blood. In exemplary embodiments, the embolization beads have a density within the range of between about 0.8 and about 2 $g/cm^3$, 0.8 and about 1.8 $g/cm^3$, 0.8 and about 1.6 $g/cm^3$, 0.8 and about 1.4 $g/cm^3$, 0.8 and about 1.2 g/cm3, between about 0.9 and about 1.1 g/cm3, between about 0.9 and about 1.0 g/cm3. Each possibility represents a separate embodiment of the invention.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

A Process for Preparing Embolization Beads Capable of Intermeshing, in Accordance with Embodiments of the Invention Analytical grade reagents including one or more of: silicon dioxide, calcium carbonate, zinc oxide, magnesium oxide, lanthanum (III) oxide, strontium carbonate, titanium dioxide and sodium carbonate are weighed and homogeneously blended. The blend is then heated to a temperature within the range of from about 1500° to 1600° C. for a time period of 30 min to 5 hours. A volume is then injected to a premade cold scaffold or mold having a predetermined shape to thereby form particulates of embolization beads having customized diameter which may vary to be between the ranges of 10 μm and 1,000 μm. The formed particulates are then extracted from the mold. The formed particulates may then be sterilized (for example, using 30 kGy gamma irradiation). In exemplary embodiments, the embolization beads are treated to incorporate a therapeutic agent within holes or a concavity shape that may be included within the protruding portions of the beads. Holes may be patched by ejector pins.

Also optionally, a radioactive isotope may be impregnated onto the embolization beads.

Example 2

Beads Coating with a Therapeutic Agent

Beads prepared as exemplified in Example 1 are coated with a desired therapeutic agent as follows: a therapeutic agent (e.g., doxorubicin) is dissolving in an appropriate solvent and admixed with the beads. The system is allowed for incubation for up to 24 hours under gentle agitation and at a temperature of 37° C. The coated beads may then be dried by an appropriate technique such as by freeze-drying.

Example 3

Therapeutic Agent Release Analysis

A beads suspension is inserted to a pre-swollen dialysis bag, the dialysis bag is clamped at both ends, and transferred to a container containing PBS. The system is allowed for incubation under gentle agitation at a temperature of 37° C.

and a sample f is taken at various time intervals to evaluate drug release under spectrophotometer.

Example 4

Beads Incorporation with a Radioisotope

Beas are incubated in a solution including a radioisotope for up to 24 hours. Following incubation, beads are washed twice with saline or PBS. Beads are centrifuged for 60 seconds at 6000 rpm, and the supernatant is removed. Each sample is then washed with 1 mL of saline and agitated for seconds. Final solutions are disposed in vials with 20 mL of scintillation liquid each, and counted for activity by a liquid scintillation analyzer.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

Each of the phrases 'consisting of' and 'consists of', as used herein, means 'including and limited to'.

The phrase 'consisting essentially of', as used herein, means that the stated entity or item (system, system unit, system sub-unit, device, assembly, sub-assembly, mechanism, structure, component, element, or, peripheral equipment, utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional 'feature or characteristic' being a system unit, system sub-unit, device, assembly, sub-assembly, mechanism, structure, component, or element, or, peripheral equipment, utility, accessory, or material, step or procedure, sub-step or sub-procedure), but only if each such additional 'feature or characteristic' does not materially alter the basic novel and inventive characteristics or special technical features, of the claimed entity or item.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably.

The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. Embolization particulates suitable for occluding a blood vessel, the embolization particulates comprising:
a plurality of embolization beads, each of said embolization beads comprises: a plurality of outwardly protruding portions, wherein, upon a first one and a second one of said embolization beads accumulating against a boundary of the blood vessel, said protruding portions of said first embolization bead are configured to intermesh with said protruding portions of said second embolization bead, so as to occlude the blood vessel; wherein said embolization beads are formed with a tetrapod shape or a tetrahedron shape; and wherein the embolization beads are configured to resist aggregation prior to reaching the blood vessel, and to aggregate within the blood vessel once delivered thereto.

2. The embolization particulates of claim 1, wherein said embolization beads are configured to resist or/and dissipate forces generated by, or originating from, fluid flow during an embolization procedure.

3. The embolization particulates of claim 1, wherein the embolization particulates are configured for laminar or/and unhindered flow there around and to diminish impact of incoming fluid flow directed thereto.

4. The embolization particulates claim 1, wherein said embolization beads have at least three outwardly protruding portions.

5. The embolization particulates of claim 1, having an elongated body extending between a first bead end and a second bead end, and wherein said protruding portions extend from at least one of said first bead end and second bead end.

6. The embolization particulates of claim 5, having four protruding portions, wherein each two protruding portions extend from first bead end and second bead end.

7. The embolization bead of claim 1, having a density within the range of between about 0.8 and about 1.6 g/cm$^3$.

8. The embolization particulates of claim 1, wherein at least one of said outwardly protruding portions includes at least one concavity; wherein said at least one concavity is filled with a therapeutic agent.

9. The embolization particulates of claim 1, wherein at least one of said outwardly protruding portions includes at least one hole passing through said outwardly protruding portion; wherein said at least one hole is filled with a therapeutic agent.

10. The embolization particulates of claim 1, wherein said embolization beads have a maximal diameter in a range of between about 5 microns and about 1,000 microns, wherein said diameter is measured between external surfaces of two opposing protruding portions of one of said embolization beads.

11. The embolization bead of claim 1, having a maximal diameter within the range of 5 microns and 500 microns.

12. The embolization particulates of claim 11, wherein said diameter is in a range of between about 5 microns and about 100 microns.

13. A composition comprising: embolization particulates according to claim 1, and a pharmaceutically acceptable excipient or carrier.

14. The composition according to claim 13, further comprising a contrasting agent or a therapeutic agent.

15. The composition according to claim 14, wherein said contrasting agent is selected from the group consisting of tantalum, tantalum oxide, and barium sulfate.

16. The composition according to claim 14, wherein said therapeutic agent is a chemotherapeutic agent.

17. A method for embolizing or occluding a blood vessel in a subject, the method comprising: injecting into the blood vessel a sufficient amount of embolization particulates according to claim 1, or a composition according to claim 13, thereby allowing said embolization beads to aggregate into a chosen aggregated structure prior to or/and during embolization.

18. The method of claim 17, wherein the blood vessel feeds a tumor or an arteriovenous malformation.

* * * * *